(12) United States Patent
Matsumura et al.

(10) Patent No.: US 12,090,459 B2
(45) Date of Patent: Sep. 17, 2024

(54) PHOTODEGRADABLE HYDROGEL

(71) Applicant: JAPAN ADVANCED INSTITUTE OF SCIENCE AND TECHNOLOGY, Ishikawa (JP)

(72) Inventors: Kazuaki Matsumura, Ishikawa (JP); Punnida Nonsuwan, Ishikawa (JP)

(73) Assignee: JAPAN ADVANCED INSTITUTE OF SCIENCE AND TECHNOLOGY, Ishikawa (JP)

( * ) Notice: Subject to any disclaimer, the term of this patent is extended or adjusted under 35 U.S.C. 154(b) by 864 days.

(21) Appl. No.: 17/261,421

(22) PCT Filed: Jul. 19, 2019

(86) PCT No.: PCT/JP2019/028531
§ 371 (c)(1),
(2) Date: Jan. 19, 2021

(87) PCT Pub. No.: WO2020/017651
PCT Pub. Date: Jan. 23, 2020

(65) Prior Publication Data
US 2021/0322944 A1    Oct. 21, 2021

(30) Foreign Application Priority Data
Jul. 20, 2018 (JP) ................. 2018-137087

(51) Int. Cl.
| | | |
|---|---|---|
| B01J 13/00 | (2006.01) | |
| A61K 31/7048 | (2006.01) | |
| A61K 41/00 | (2020.01) | |
| C08J 3/21 | (2006.01) | |
| C08J 3/24 | (2006.01) | |
| A61K 9/06 | (2006.01) | |

(52) U.S. Cl.
CPC ....... B01J 13/0065 (2013.01); A61K 31/7048 (2013.01); A61K 41/0042 (2013.01); C08J 3/212 (2013.01); C08J 3/24 (2013.01); A61K 9/06 (2013.01); C08J 2305/00 (2013.01); C08J 2479/02 (2013.01)

(58) Field of Classification Search
None
See application file for complete search history.

(56) References Cited

U.S. PATENT DOCUMENTS

2008/0319101 A1   12/2008   Nakajima et al.
2019/0062462 A1*   2/2019   Shi .................. C08G 69/10

FOREIGN PATENT DOCUMENTS

| EP | 1 849 486 | 10/2007 |
|---|---|---|
| EP | 2 100 628 | 9/2009 |
| JP | WO2006/080523 | 8/2006 |
| JP | WO2008/066182 | 6/2008 |
| JP | 2015-48467 | 3/2015 |
| JP | 2018-39886 | 3/2018 |
| WO | 2006/080523 | 8/2006 |
| WO | 2008/066182 | 6/2008 |

OTHER PUBLICATIONS

Wang et al. A Polydopamine Nanoparticle-Knotted Poly(ethylene glycol) Hydrogel for On-Demand Drug Delivery and Chemo-photothermal Therapy. Chem. Mater. 2017, 29, 1370-1376. Jan. 11, 2017. (Year: 2017).*
Shen et al. Fabrication of polydopamine nanoparticles knotted alginate scaffolds and their properties. J. Biomed. Res. Part A, 2018, 106A, 3255-3266.Published online Sep. 22, 2018. (Year: 2018).*
Panao et al. Ultra-absorbent hybrid hydrogel based on alginate and SiO2 microspheres: A high-water-content system for removal of methylene blue. Journal of Molecular Liquids, 2019, 276, 204-213. Available online Nov. 30, 2018. (Year: 2018).*
Wu et al., "An Injectable Supramolecular Polymer Nanocomposite Hydrogel for Prevention of Breast Cancer Recurrence with Theranostic and Mammoplastic Functions", Advanced Functional Materials, 2018, vol. 28, pp. 1-12.
Han et al., "Polydopamine Nanoparticles Modulating Stimuli-Responsive PNIPAM Hydrogels with Cell/Tissue Adhesiveness", ACS Applied Materials & Interfaces, 2016, vol. 8, pp. 29088-29100.
Hu et al., "A thermo-degradable hydrogel with light-tunable degradation and drug release", Biomaterials, 2017, vol. 112, pp. 133-140.
International Search Report issued Sep. 10, 2019 in International (PCT) Application No. PCT/JP2019/028531, with English translation.

* cited by examiner

*Primary Examiner* — Stephen E Rieth
(74) *Attorney, Agent, or Firm* — Wenderoth, Lind & Ponack, L.L.P.

(57) ABSTRACT

A hydrogel of which the degradation is accurately controlled can be provided by a photodegradable hydrogel production method, the method comprising the steps of: reacting α-glucan having a weight average molecular weight of 2000 to 200,000 with a compound represented by formula I to introduce a group represented by formula II into the α-glucan; oxidizing the α-glucan having, introduced therein, the group represented by formula II with periodic acid or a periodate salt to introduce an aldehyde group into the α-glucan; and adding aminated carrageenan gel beads having polydopamine particles embedded therein to a gelling agent which has been prepared by introducing a group represented by formula II and an aldehyde group into α-glucan, and then causing the crosslinking reaction of the resultant product with a polythiol-type reducing agent to form the hydrogel.

10 Claims, 16 Drawing Sheets

PHOTODEGRADABLE HYDROGEL

FIELD OF THE INVENTION

The present invention relates to a photodegradable hydrogel.

BACKGROUND OF THE INVENTION

Degradable hydrogels or gelling agents have been developed as adhesives for medical use, especially for surgery (Patent Literatures 1 and 2). Such medical adhesives are used for adhesion, filling, synechia prevention, hemostasis and the like of biological tissues. These hydrogels for medical adhesives are required to be appropriately decomposed in vivo after accomplishing their purposes.

Further, such hydrogels are also used as substrates for drug delivery, and for example, protein gels such as gelatin and polysaccharide gels such as hyaluronic acid and alginic acid are known. These hydrogels for DDS substrates are also required to be properly decomposed in vivo for drug releasing.

Patent Literature 3 discloses a hydrogel that can be decomposed in vivo.

CITATION LIST

Patent Literatures

[Patent Literature 1] WO 2008/066182 A1
[Patent Literature 2] WO 2006/080523 A1
[Patent Literature 3] Japanese Patent Application Publication No. 2018-39886 A

SUMMARY OF THE INVENTION

Technical Problem

If more precise decomposition control of hydrogels that can be decomposed in vivo becomes possible, this would enable more precise control of drug release.

Therefore, an object of the present invention is to provide a hydrogel with more precisely controlled decomposition.

Solution to Problem

As a result of intensive studies, the present inventors have obtained an idea of controlling decomposition of a hydrogel by using light irradiation as a trigger for starting the decomposition. The present inventors have then found that the above object could be achieved by a photodegradable hydrogel as described later, and have arrived at the present invention.

Thus, the present invention includes the following aspects (1) to (10):

(1)
A method for producing a photodegradable hydrogel, comprising the steps of:
  allowing α-glucan having a weight average molecular weight in a range of from 2,000 to 200,000 to react with a compound represented by the following formula I:

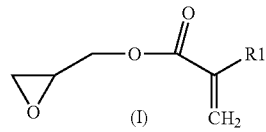

(formula I)

in which the R1 group is a C1-C3 alkyl group,
to introduce at least one group represented by the following formula II:

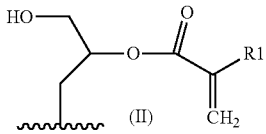

(formula II)

in which the R1 group is the same group as the R1 group in the formula I,
into the α-glucan;
  oxidizing the α-glucan having the introduced group represented by the formula II with periodic acid or a periodate to introduce at least one aldehyde group into the α-glucan; and
  adding aminated carrageenan gel beads with embedded polydopamine particles to a gelling agent obtained by introducing the group represented by the formula II and the aldehyde group into the α-glucan, and causing a crosslinking reaction with a polythiol reducing agent to form a hydrogel.

(2)
The method according to (1), wherein the aminated carrageenan gel beads with dispersively embedded polydopamine particles are prepared by a method comprising a step of adding to an aqueous solution of aminated carrageenan an aqueous solution of potassium salt, sodium salt or calcium salt wherein polydopamine particles are dispersed.

(3)
The method according to (1) or (2), wherein the step of adding the aminated carrageenan gel beads with embedded polydopamine particles to the gelling agent obtained by introducing the group represented by the formula II and the aldehyde group into the α-glucan, and causing the crosslinking reaction with the polythiol reducing agent to form the hydrogel is a step of adding a drug and the aminated carrageenan gel beads with embedded polydopamine particles to the gelling agent obtained by introducing the group represented by the formula II and the aldehyde group into the α-glucan, and causing the crosslinking reaction with the polythiol reducing agent to form the hydrogel.

(4)
A method for photodegrading a hydrogel, comprising irradiating the photodegradable hydrogel produced by the method according to any one of (1) to (3) with light.

(5)
A method for photo-releasing a drug from a hydrogel, comprising irradiating the photodegradable hydrogel produced by the method according to (3) with light.

(6)
A hydrogel having a modified α-glucan crosslinked by dithiothreitol, the modified α-glucan comprising:

at least one group represented by the following formula II:

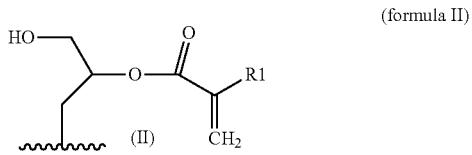

(formula II)

in which the R1 group is a C1-C3 alkyl group,
the at least one group represented by the formula II being introduced into α-glucan having a weight average molecular weight in a range of from 2,000 to 200,000 at a degree of substitution in a range of from 10 to 50% per glucose unit of the α-glucan, wherein H of an OH group in the α-glucan is substituted with the group represented by the formula II; and
at least one aldehyde group resulting from oxidation of periodic acid, the at least one aldehyde group being introduced at a degree of substitution in a range of from 25 to 75% per glucose unit of the α-glucan,
wherein aminated carrageenan gel beads with embedded polydopamine particles are embedded in the hydrogel.

(7)
The hydrogel according to (6), wherein a drug is embedded.

(8)
The hydrogel according to (6) or (7), wherein the α-glucan having the weight average molecular weight in the range of from 2,000 to 200,000 is dextran.

(9)
An additive for photodegradable hydrogels, the additive comprising aminated carrageenan gel beads with embedded polydopamine particles.

(10)
A method for producing an additive for photodegradable hydrogels, the method comprising a step of adding an aqueous solution of potassium salt, sodium salt or calcium salt in which polydopamine particles are dispersed to an aqueous solution of aminated carrageenan.

Advantageous Effects of Invention

The present invention provides a photodegradable hydrogel. According to the present invention, decomposition control of a hydrogel can be carried out by using light irradiation as a trigger for starting of decomposition.

DETAILED DESCRIPTION OF THE INVENTION

Figure 1:
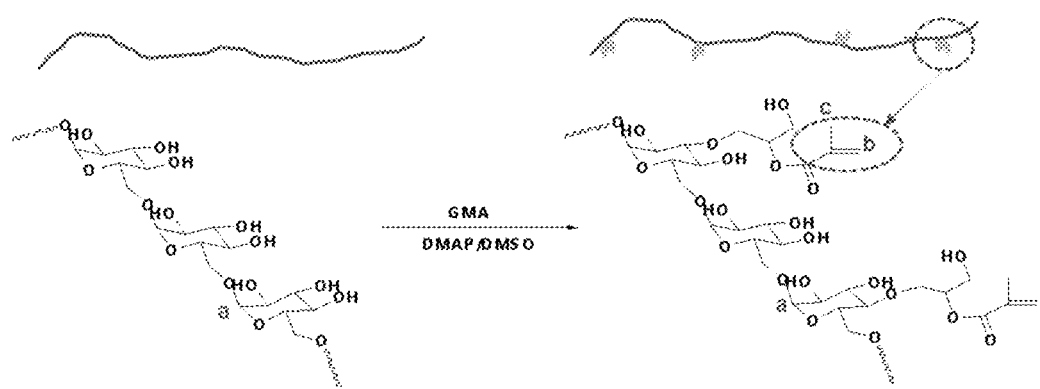
FIG. 1 is an explanatory view of a reaction of Dex-GMA synthesis.

The present invention will be described in detail below with reference to specific embodiments. The present invention is not limited to the specific embodiments listed below.
[Production of Photodegradable Hydrogel]
A photodegradable hydrogel according to the present invention can be produced by a method for producing a photodegradable hydrogel, comprising the steps of:
allowing α-glucan having a weight average molecular weight in a range of from 2,000 to 200,000 to react with a compound represented by the following formula I:

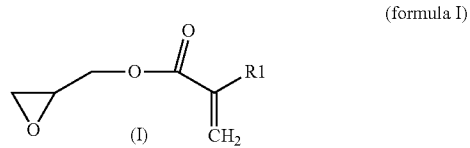

(formula I)

in which the R1 group is a C1-C3 alkyl group,
to introduce at least one group represented by the following formula II:

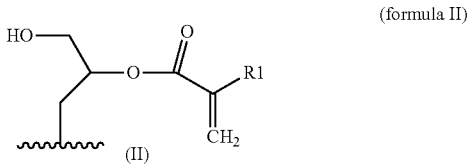

(formula II)

in which the R1 group is the same group as the R1 group in the formula I,
into the α-glucan;
oxidizing the α-glucan having the introduced group represented by the formula II with periodic acid or a periodate to introduce at least one aldehyde group into the α-glucan; and adding aminated carrageenan gel beads with embedded polydopamine particles to a gelling agent obtained by introducing the group represented by the formula II and the aldehyde group into the α-glucan, and causing a crosslinking reaction with a polythiol reducing agent to form a hydrogel.

[α-Glucan]

The α-glucan is a sugar chain (polysaccharide) in which glucoses are subjected to dehydration condensation and linked together by a bonds. Examples include dextran, dextrin, and pullulan. In a preferred embodiment, α-glucan having a weight average molecular weight in a range of, for example, from 2,000 to 200,000, or from 8,000 to 150,000, or 10,000 to 100,000, can be used. In a preferred embodiment, dextran having a weight average molecular weight in the above range can be used. The weight average molecular weight can be determined by a general aqueous GPC (gel permeation chromatography) measurement. More particularly, it can be measured as disclosed in Examples. Examples of commercially available dextran that can be used include a medical grade product commercially available from Pharmacosmos A/S, or a product available from FUJIFILM Wako Pure Chemical Corporation, or the like.

[Compound of Formula I]

In the compound of the formula I, the R1 group can be, for example, a C1-C3 alkyl group, or a C1-C2 alkyl group, for example, a methyl group or an ethyl group. In a preferred embodiment, the compound of formula I can be glycidyl methacrylate (GMA) or glycidyl acrylate.

[Introduction of Group of Formula II]

The groups of the formula II to be introduced into α-glucan by the compound of formula I are introduced by substituting H of an OH group of a glucose unit of the α-glucan. A degree of substitution (DS %) of the groups can be determined by $^1$H-NMR measurement as an introduction rate (%) of the groups of the formula II per glucose unit of α-glucan. The degree of substitution of the groups of the formula II per glucose unit can be, for example, in a range of from 10 to 50%, or in a range of from 20 to 40%. In addition, when conversion is made such that the glucose units into which the groups of the formula II are introduced and the glucose units into which the groups are not introduced undergo cleavage by the oxidation with periodic acid at the same ratio, the degree of substitution per glucose unit remaining after the oxidation with periodic acid will be in the same range as described above.

The reaction of introducing the groups of the formula II by the reaction of the α-glucan with the compound of the formula I can be carried out under general reaction conditions of, for example, glycidyl methacrylate (GMA) with a hydroxyl group. For example, it can be carried out by heating, for example in a nitrogen atmosphere, in the presence of dimethyl sulfoxide (DMSO) and dimethylaminopyridine (DMAP).

[Oxidation with Periodic Acid]

The α-glucan with the introduced groups represented by the formula II is oxidized with periodic acid or periodate to introduce aldehyde groups into the α-glucan. The oxidation with periodic acid can be carried out under conditions for a general oxidation method with periodic acid.

[Introduction of Aldehyde Group]

The aldehyde groups are introduced by cleaving the glucose units of α-glucan by the oxidation with periodic acid. A degree of substitution (DS %) of the groups can be determined as an introduction rate (%) of the aldehyde groups per glucose unit of the α-glucan by $^1$H-NMR measurement. The degree of substitution (%) of the aldehyde groups per glucose unit of the α-glucan can be, for example, in a range of from 20 to 80%, in a range of from 25 to 75%, or in a range of from 40 to 60%. Alternatively, this value can be converted as the degree of substitution of the aldehyde groups per glucose unit remaining after undergoing the oxidation with periodic acid. In this case, the degree of substitution of the aldehyde groups per remaining glucose unit can be, for example, in a range of from 22 (22.2) to 133%, in a range of from 29 (28.6) to 120%, or in a range of from 50 to 85.7 (86) %.

[Crossing Reaction]

A modified α-glucan compound (gelling agent) obtained by introducing the groups represented by the formula II and the aldehyde groups into the α-glucan can be crosslinked with a polythiol reducing agent to form a hydrogel. Examples of the polythiol reducing agent include polythiol alcohol and polythiol, for examples, dithiol alcohol and dithiol. Specific examples include DTT (dithiothreitol), 1,4-butanedithiol, ethanethiol, and 1,1-propanedithiol. The SH group of the polythiol reducing agent can undergo a Michael addition reaction with the group of the formula II without any catalyst. This can lead to crosslinking of the molecules of the modified α-glucan compound to form a hydrogel. This reaction is an irreversible reaction, and no decomposition occurs as it is.

[Stability of Hydrogel]

The hydrogel with the crosslinked α-glucan compounds is stable in that the formed crosslinks are not decomposed as they are. For example, about 80 percent of the gel is maintained even if the gel is maintained in PBS (phosphate buffered saline) at 37° C. for 8 days.

[Degradability of Hydrogel]

The introduced aldehyde groups are retained in the hydrogel with the crosslinked α-glucan compounds without being used in the crosslinking reaction. Then, when amino groups are allowed to react with the aldehyde groups, the main chain of the α-glucan structure is cleaved to generate fragmentation accompanied by a decrease in a molecular weight, and as a result, the hydrogel is decomposed. That is, the decomposition can be controlled by allowing the introduced aldehyde groups to react with the amino groups.

[Aminated Carrageenan Gel Beads with Embedded Polydopamine Particles]

In the step of forming the hydrogel, the aminated carrageenan gel beads with embedded polydopamine particles are added to the gelling agent in which the groups represented by the formula II and the aldehyde groups have been introduced into the α-glucan, prior to the crosslinking reaction.

In a preferred embodiment, an addition amount of the aminated carrageenan gel beads with the embedded polydopamine particles can be, for example, in a range of from 10 to 60%, and preferably in a range of from 20 to 50%, as a dry mass of the aminated carrageenan added to the gelling agent in which the groups represented by the formula II and the aldehyde groups have been introduced into the α-glucan. In a preferred embodiment, the content of the aminated carrageenan gel beads with the embedded polydopamine particles can be, for example, in a range of from 0.1% to 10%, and preferably in a range of from 0.5% to 2.0%, as the dry mass of the added aminated carrageenan, based on a wet mass of the entire photodegradable hydrogel.

The gel beads can be produced, for example, by adding an aqueous solution of potassium salt, sodium salt or calcium salt in which polydopamine particles are dispersed to an aqueous solution of aminated carrageenan. The addition can be carried out, for example, by dropping. This can allow the aminated carrageenan gel with the embedded polydopamine particles to be obtained in the form of gel beads. If desired, the gel beads can be dried by a means such as freeze-drying and used for subsequent addition. In a preferred embodiment, the gel beads can be obtained, for example, as particles having a particle diameter of from 500 to 2000 μm, and preferably from 800 to 1500 μm.

For example, the aqueous solution of the aminated carrageenan can have an aminated carrageenan concentration in a range of from 0.5 to 10% by mass, and preferably in a range of from 1 to 8% by mass, and more preferably in a range of from 2 to 6% by mass, and still more preferably in a range of from 3 to 5% by mass. Examples of the aminated carrageenan that can be used include aminated κ-carrageenan.

The amino groups can be introduced into the carrageenan by known means. In a preferred embodiment, the amino groups can be introduced into the carrageenan by the means as described in Examples. In the aminated carrageenan, the degree of substitution of the amino groups in the carrageenan can be in a range of, for example, from 0.1 to 5.0%, and preferably from 0.5 to 2.0%, per repeating unit. The degree of substitution can be determined based on the TNBS method as described in Examples.

The aqueous solution of potassium salt, sodium salt or calcium salt can have a salt concentration, for example, in a range of from 1 to 20% by mass, and preferably in a range of from 2 to 12% by mass, and more preferably in a range of from 2 to 10% by mass, and still more preferably in a range of from 3 to 8% by mass. Examples of potassium salt that can be used include potassium chloride and potassium bromide.

[Polydopamine Particles]

Polydopamine is a multimer derived from dopamine and can be prepared by known means. In a preferred embodiment, it can be synthesized according to the scheme as described in Examples. In a preferred embodiment, the polydopamine can be obtained as black spherical particles which can have a particle diameter, for example, in a range of from 50 to 500 μm, and preferably from 100 to 300 μm.

In a preferred embodiment, the polydopamine particles are dispersed and embedded in the aminated carrageenan gel beads. The content of the polydopamine particles in the aminated carrageenan gel beads can be, for example, in a range of from 1.0 to 20%, and preferably in a range of from 5.0 to 10%, based on the dry mass of the gel beads.

[Photodegradation of Photodegradable Hydrogel]

For the photodegradable hydrogel, the decomposition of the hydrogel is started using light irradiation as a trigger. For this mechanism, the present inventors believe that once the irradiated light reaches the polydopamine, this causes the aminated carrageenan gel to initiate a local structural change due to heat, whereby the amino groups buried in the aminated carrageenan gel are exposed and react with the aldehyde groups introduced into the hydrogel to cleave the main chain of the α-glucan structure and lead to fragmentation accompanied by a decrease in a molecular weight, resulting in the decomposition of the hydrogel.

[Light Irradiation]

In a preferred embodiment, a wavelength of the irradiated light for photodecomposition can be, for example, in a range of from 600 to 2000 nm, preferably in a range of from 750 to 1200 nm. As light for irradiation, near-infrared light (NIR) can be used, and the wavelength of this light is said to have no adverse effect on the human body, and at the same time, has a certain degree of transparency to the human body. Therefore, the NIR can be suitably used in an embodiment where after the photodegradable hydrogel is embedded in a tissue, the irradiation with near infrared light starts the decomposition of the hydrogel triggered by the light irradiation to release a drug contained in the hydrogel.

[Drug]

In a preferred embodiment, the photodegradable hydrogel can be used to contain a drug therein and release the drug by degradation initiated using light irradiation as a trigger. The drug can be embedded in the photodegradable hydrogel by adding the drug at or before or after the addition of the aminated carrageenan gel beads with the embedded polydopamine particles, for example during the gel formation of the photodegradable hydrogel, and then causing the crosslinking reaction. The drug contained in the photodegradable hydrogel is not particularly limited. For example, a hydrophobic drag can be preferably used. Examples of the drug include antibacterial agents such as amphotericin B, non-steroidal anti-inflammatory drugs such as ibuprofen, peptides such as basic fibroblast growth factors, taxol, doxorubicin, and salts and hydrates thereof.

[Photodegradable Hydrogel]

Since the photodegradable hydrogel according to the present invention is based on the α-glucan, it has higher biocompatibility and improved photodegradability, so that it can be suitably used as a medical adhesive and a DDS substrate. The present invention also relates to a method for photodegrading the photodegradable hydrogel by irradiating it with light, and a method for photo-releasing the drug by irradiating the photodegradable hydrogel with the embedded drug with light, and a drug delivery system (DDS) that is photo-releasable of the drug using light irradiation as a trigger.

EXAMPLES

Hereinafter, the present invention will be described in detail with reference to Examples. The present invention is not limited to Examples illustrated below. In Examples, "%" and "parts" indicate % by weight and parts by weight, respectively, unless otherwise specified.

Experimental Example 1

[Synthesis of Glycidyl Methacrylate-Introduced Dextran (Dex-GMA)]

Five gram (g) of dextran (Meito Sangyo Co., Ltd., a molecular weight of 70,000) was dissolved in 20 mL of dimethyl sulfoxide (DMSO), and nitrogen gas was blown into the solution for 30 minutes. To the solution were added 4.8 g of dimethylaminopyridine (DMAP) and 2.3 g of glycidyl methacrylate (GMA), and allowed to react in a nitrogen atmosphere for 30 minutes. The solution was heated to 50° C. and further allowed to react for 12 hours, after which HCl was added to neutralize DMAP and stop the reaction. The solution was dialyzed against distilled water for one week with a dialysis membrane (Spectra/Por) of MWCO=3500, and reacted dextran (Dex-GMA) was purified and recovered by freeze-drying. The obtained Dex-GMA was characterized by FTIR and $^1$H-NMR.

In the FTIR chart, the introduction of GMA was qualitatively confirmed from a C=O band newly appearing around 1707 $cm^{-1}$, and the degree of substitution (DS) was calculated from a ratio of a peak of a vinyl proton (6.32-6.34 ppm) to a peak of an anomeric proton (5.08 ppm) in the $^1$H-NMR spectrum. As a result, DS was 29% (per glucose unit).

Figure 2:
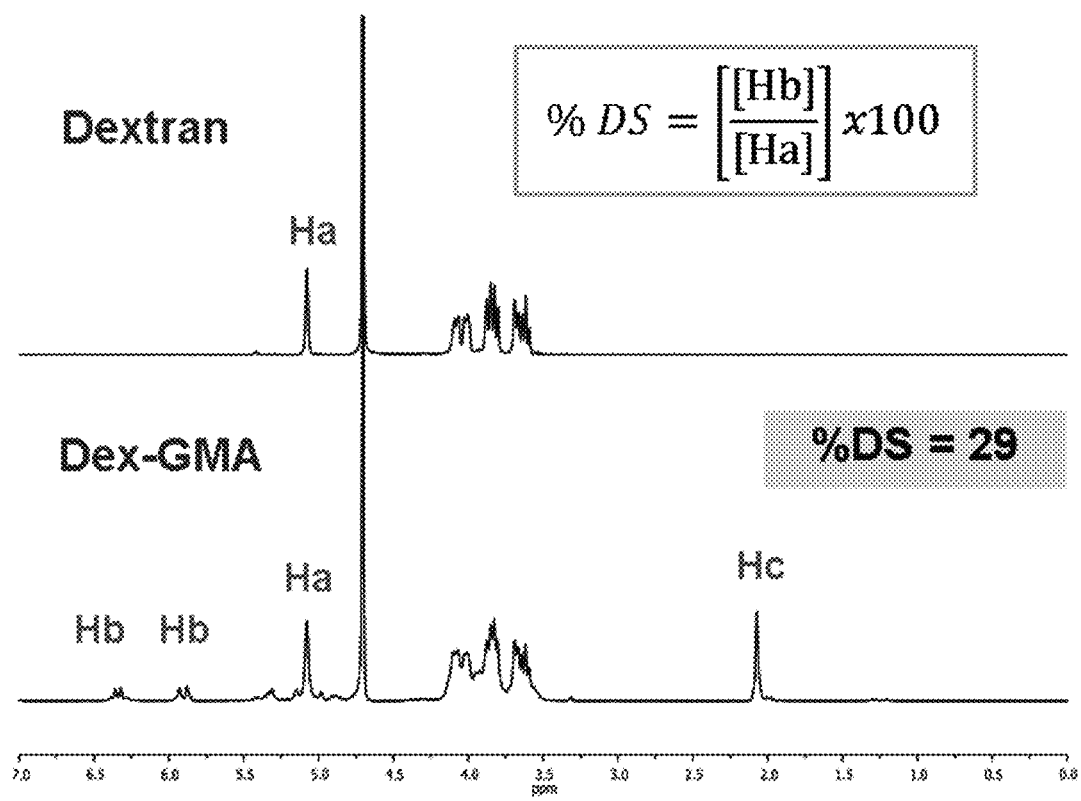
FIG. 2 is a chart showing results of $^1$H-NMR measurement.

The reaction of Dex-GMA synthesis as described above is shown in FIG. 1. The results of the above $^1$H-NMR measurement are shown in FIG. 2. The degree of substitution (DS) of GMA as described above was calculated from the peak of the $^1$H-NMR spectrum by the equation: DS (%)= ([Hb]/[Ha])×100(%).

Experimental Example 2

[Synthesis of Ox-Dex-GMA]

Oxidized Dex-GMA (Ox-Dex-GMA) was synthesized by the following method:

2.5 g of Dex-GMA prepared in Experimental Example 1 was dissolved in 20 mL of distilled water, mixed with 20 mL of distilled water in which 0.75 g of sodium periodate was dissolved, and allowed to react at 50° C. for one hour. After the reaction, the solution was dialyzed against distilled water with a dialysis membrane of MWCO 3500 for one day, and Ox-Dex-GMA was recovered by freeze-drying. The characterization was performed by $^1$H-NMR. The introduction of aldehyde was confirmed by $^1$H-NMR as an aldehyde peak at 9.64 ppm. An amount of aldehyde groups introduced was quantified by detecting fluorescence due to the reaction of acetanilide (AAA) with aldehyde in the presence of ammonia (Li et al., Analytical Sciences, 2007, 23, 1810-1860). As a result, The DS (degree of substitution) was 51%.

Figure 3:
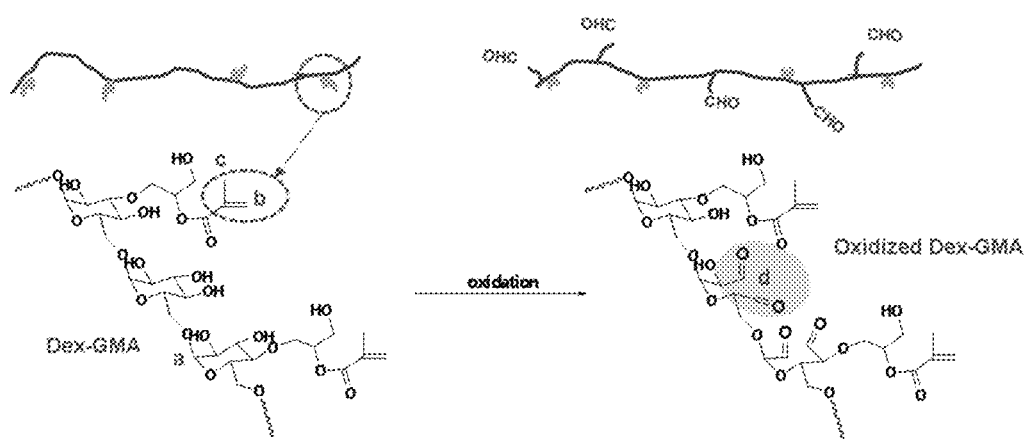
FIG. 3 is an explanatory view of a reaction of Ox-Dex-GMA synthesis.
Figure 4:
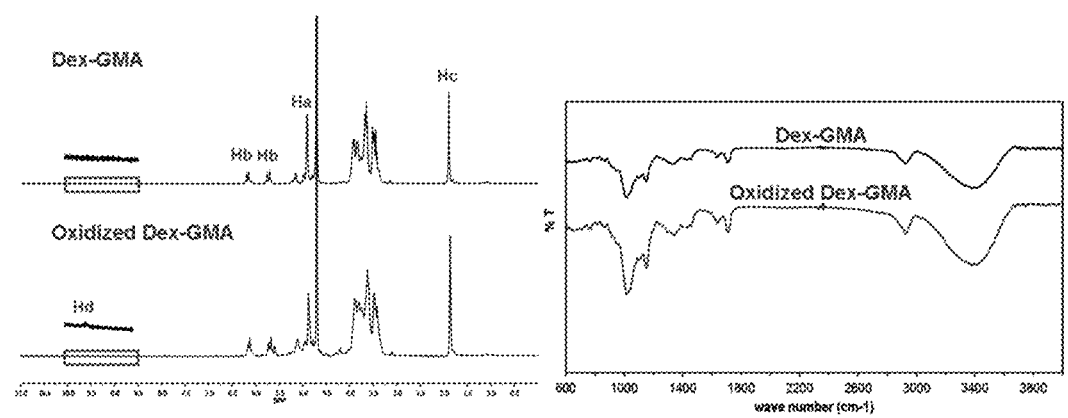
FIG. 4 is a chart showing results of $^1$H-NMR measurement and results of FTIR measurement.

The reaction of the Ox-Dex-GMA synthesis as described above is shown in FIG. 3. The results of the above $^1$H-NMR measurement and the results of the above FTIR measurement are summarized in FIG. 4. The degree of substitution (DS) of the aldehyde groups was determined by the equation: DS (%)=([Hd]/[Ha])×100(%) in $^1$H-NMR shown in FIG. 4.

Experimental Example 3

[Gelation by Reaction of Ox-Dex-GMA with DTT]

By mixing 0.1 mL of each of 10 wt % Ox-Dex-GMA aqueous solution and 1.36 wt % DTT aqueous solution, gelation was confirmed at 37° C. in 45 minutes. The gelation time when 0.2 mL of Ox-Dex-GMA was used was 10 hours and 40 minutes, while the gelation time when 0.2 mL of DTT was used was 20 minutes. These gels were stable in PBS without decomposition.

Figure 5:
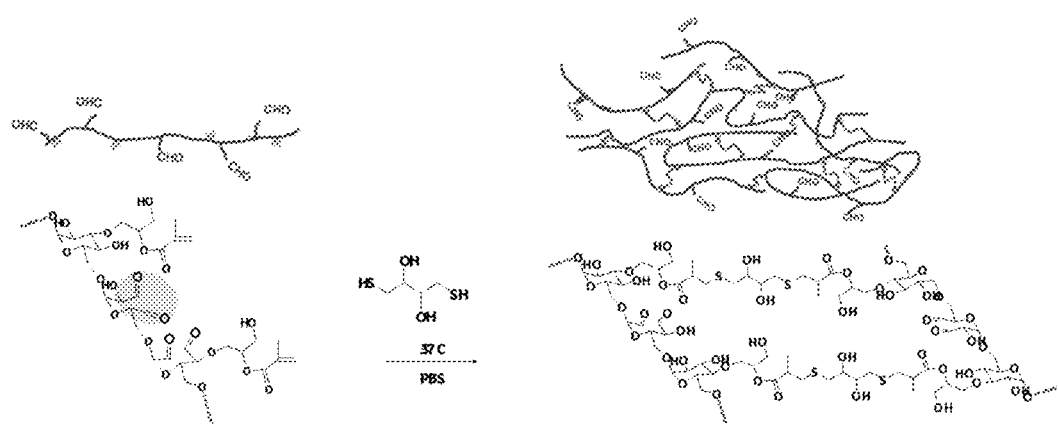
FIG. 5 is an explanatory view of a gelation reaction of Ox-Dex-GMA.

The gelation reaction of Ox-Dex-GMA as described above is shown in FIG. 5.

Experimental Example 4

[Synthesis of Aminated κ-Carrageenan]

Aminated κ-carrageenan (amino-CG) was synthesized from carrageenan (CG) as follows: 1 g of κ (kappa)-carrageenan (Tokyo Chemical Industry, Co., Ltd.) was dispersed in 10 mL of 2-propanol in a 100 mL eggplant-shaped flask, and 1.2 mL of a solution of 40% NaOH was slowly dropped at 40° C., and then refluxed for one hour to cause a reaction. Subsequently, 0.547 g of 3-bromopropylamine was added, and allowed to react at 50° C. for 24 hours. At the end of the reaction, the solution was neutralized with 1 M hydrochloric acid, the resulting precipitate was collected with a filter and washed with 2-propanol, and aminated carrageenan was recovered by freeze-drying. The characterization was performed by $^1$H-NMR and FTIR. In $^1$H-NMR, a peak due to a methylene proton adjacent to the amino group could be confirmed at around 1.5 to 2.25 ppm. In the FTIR spectrum, a new band due to a primary amine could be confirmed at around 1563 cm$^{-1}$. The DS was determined by the TNBS method (Means G R et al., Amino groups. In Chemical Modification of Proteins, Holden-Day, Inc.: San Francisco, 1971, pp. 214-217), which is a method for quantifying amino groups. As a result, the DS was 0.87% based on the repeating unit conversion.

Figure 6:
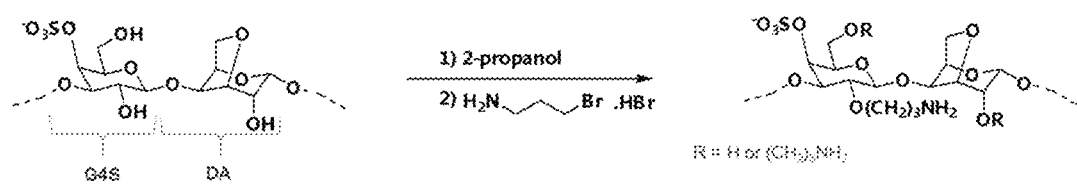
FIG. 6 is an explanatory view of a reaction of aminated κ-carrageenan synthesis.

The reaction for the synthesis of the above aminated κ-carrageenan is shown in FIG. 6.

Experimental Example 5

[Preparation of PDA Particles]

Polydopamine (PDA) particles were prepared by dissolving 0.3 g of dopamine hydrochloride in 5 mL of distilled water, mixing it with a mixed solution of 1 mL of 29% aqueous ammonia, 20 mL of ethanol, and 45 mL of distilled water, and allowing the mixture to react with stirring for 12 hours. After the preparation, the PDA particles were filtered, washed with distilled water, and then dried. The measurement of UV absorption confirmed absorption in a wide range of from 200 to 800 nm or more.

Figure 7:
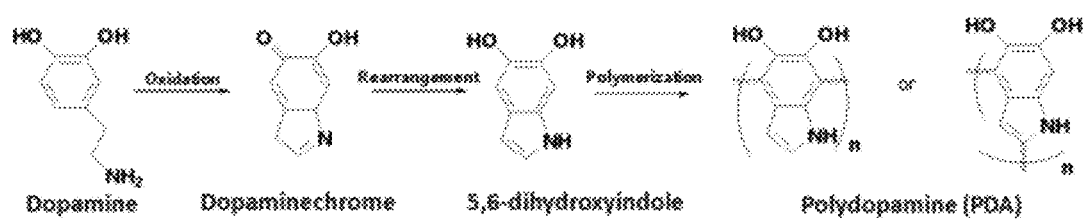
FIG. 7 is an explanatory view of a scheme for synthesizing polydopamine from dopamine.
Figure 8:
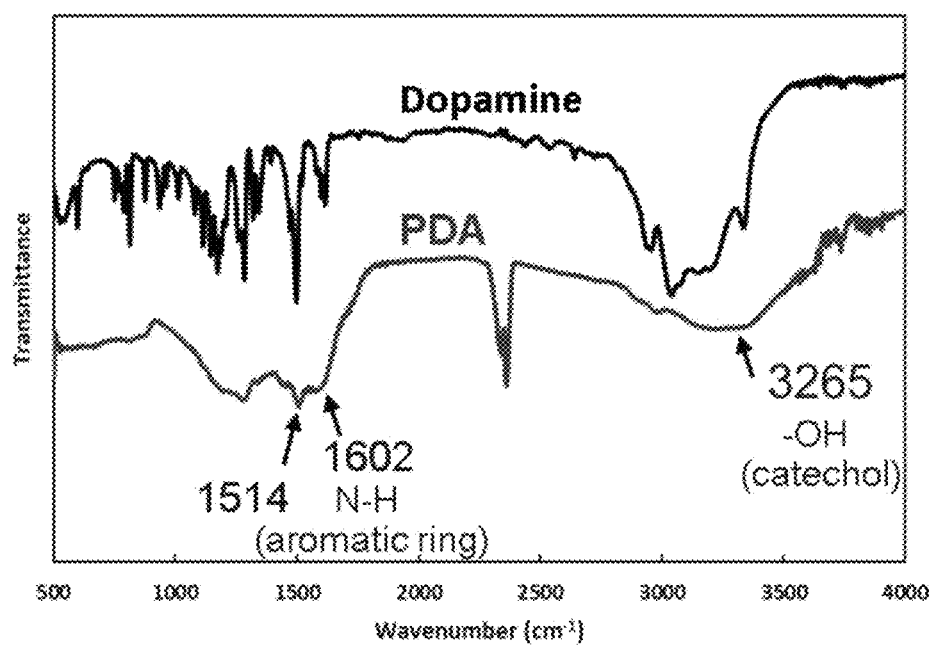
FIG. 8 is a chart showing results of FTIR measurement.
Figure 9:
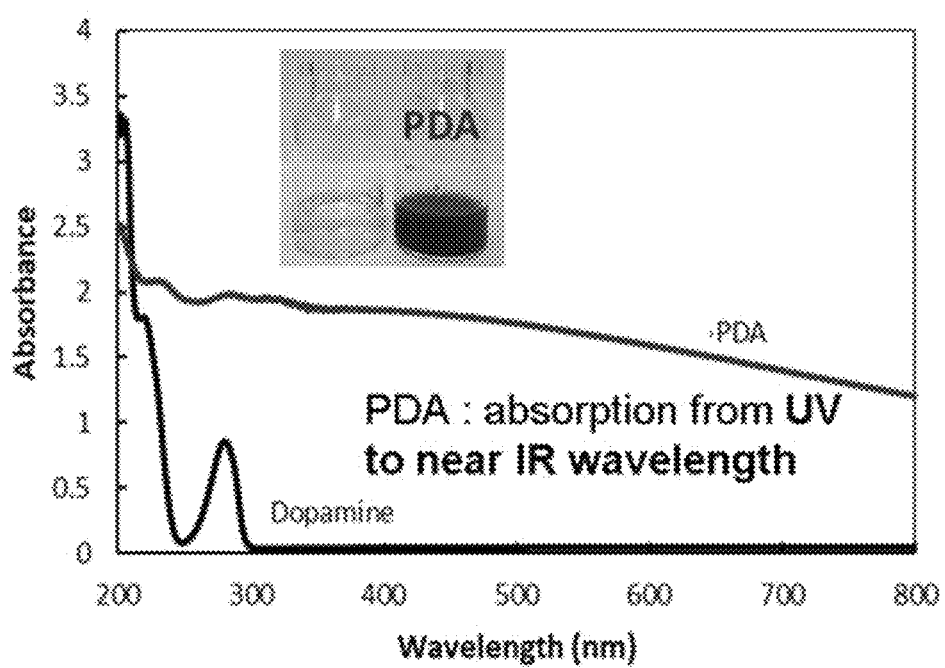
FIG. 9 is an explanatory view showing results of measurement of UV absorption.
Figure 10:
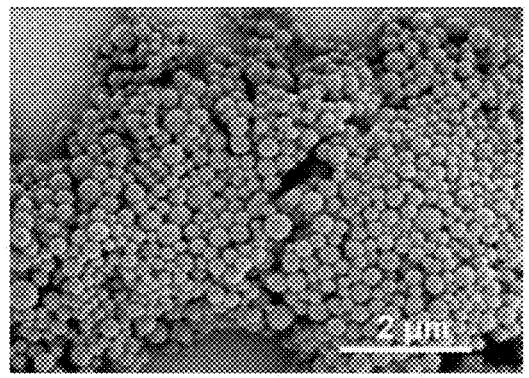
FIG. 10 is an electron micrograph of PDA particles.
Figure 11:
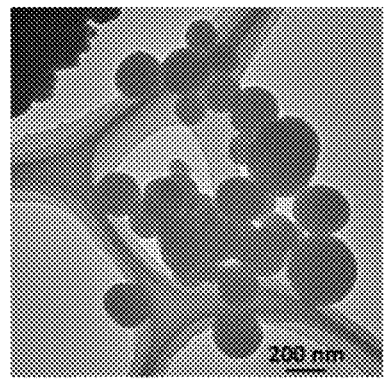
FIG. 11 is an electron micrograph of PDA particles.

FIG. 7 shows a scheme for synthesizing polydopamine from dopamine. FIG. 8 shows the results of FTIR measurement. FIG. 9 shows the measured results of UV absorption. As can be seen from the photograph shown in the graph of FIG. 9, the dopamine solution was colorless and transparent, and the dispersion of PDA was a black suspension. FIGS. 10 and 11 show electron micrographs of PDA particles. As shown in the electron micrograph, the PDA particles presents very ordered spheres, and many of them had a particle diameter of from about 100 to about 300 μm.

Experimental Example 6

[Preparation of PDA-Containing Aminated Carrageenan Composite Gel Beads]

A 4% aqueous carrageenan solution was dropped into a 5% KCl aqueous solution containing 0.02% PDA, and allowed to react at room temperature for 30 minutes with stirring to obtain gel beads. The obtained gel beads were washed with distilled water, freeze-dried, and used as dried gel beads for the subsequent operation.

Figure 12:
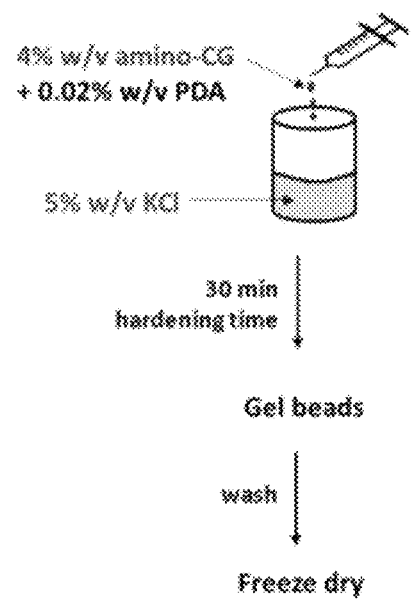
FIG. 12 is an explanatory view of an operation procedure for obtaining dried gel beads of PDA-containing aminated carrageenan.
Figure 13:
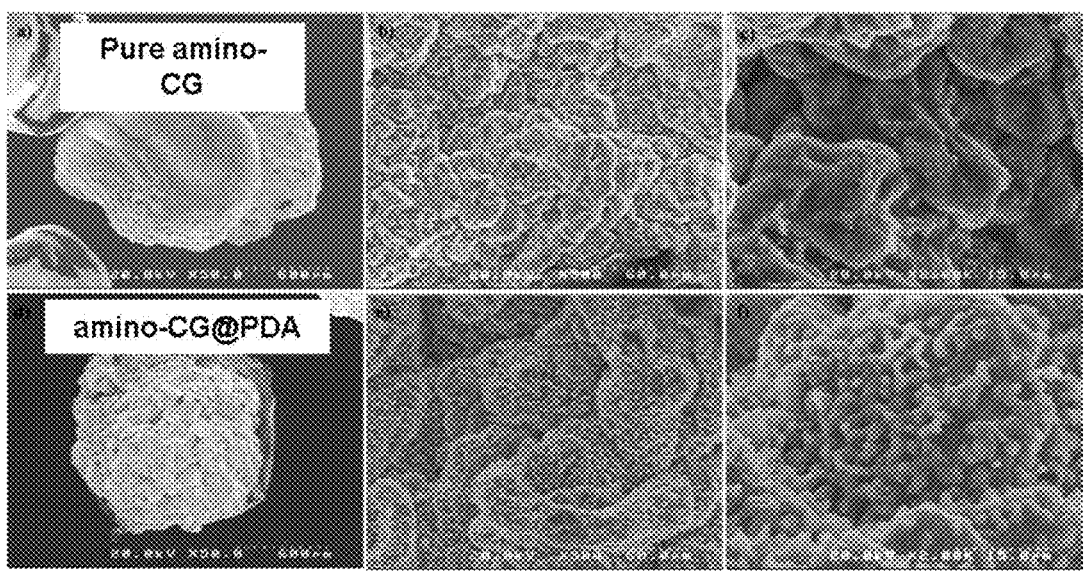
FIG. 13 is electron micrographs of dried gel beads of PDA-containing aminated carrageenan.

FIG. 12 shows an explanatory view of an operation procedure for obtaining dried gel beads. FIG. 13 shows electron micrographs of the obtained dried gel beads of PDA-containing aminated carrageenan (three photographs in the lower column of FIG. 13, "amino-CG@PDA"). For comparison, electron micrographs of dried gel beads prepared using a 4% amination carrageenan aqueous solution and a 5% KCl aqueous solution containing no PDA are also shown (three photographs in the upper column of FIG. 13, "Pure amino-CG").

Experimental Example 7

[NIR Responsive Dissolution]

The dried gel beads of PDA-containing aminated carrageenan were sampled in an amount of 0.01 g, added to 5 mL of PBS, and irradiated with NIR (808 nm, 1 W/cm$^2$) laser at room temperature to confirm the dissolution of the gel. The solubility of the gel was determined by measuring the amount of amino groups in the supernatant by the TNBS method. In the case of no NIR irradiation, the dissolution was 5% or less even after 5 hours, whereas the on/off of the NIR laser was repeated for 30 minutes, thereby confirming that substantially all the gels were dissolved after 5 hours.

Experimental Example 8

[Drug Release Control from Dextran Gel by NIR Irradiation]

Doxorubicin hydrochloride was dissolved in a solution of 10% oxidized dextran GMA (Ox-Dex-GMA) in PBS such that the former had a concentration of 0.05 mg/mL. Further, 0.01 g of dried gel beads of PDA-containing aminated carrageenan were added, and after 30 minutes, a 1.36% DTT/PBS solution was mixed and left at 37° C. for 30 minutes to cause gelation. A hydrogel having the PDA-containing aminated carrageenan composite gel beads embedded in a hydrogel containing doxorubicin hydrochloride (DOX) was thus obtained.

To the gel was added 5 mL of PBS and irradiated with NIR laser at 808 nm (1 W/cm$^{-2}$). The irradiation was continuously carried out for 30 minutes, and no irradiation was carried out for the subsequent 30 minutes. Five sets of the irradiation were carried out, and a doxorubicin concentration of the supernatant was periodically measured from the fluorescence intensity.

As a result, 3% of doxorubicin was eluted by the first irradiation for 30 minutes. On the other hand, in the system that did not carry out the irradiation, the released amount was about 0.1%. This would be because the aminated carrageenan was eluted by the irradiation with NIR, the eluted aminated carrageenan reacted with the aldehyde in the gel to cause decomposition of the gel, so that the doxorubicin which was the supported drug was eluted. After 5 hours, the released rate reached 5.5% for the irradiated system and 0.9% for the non-irradiated system.

Figure 14:
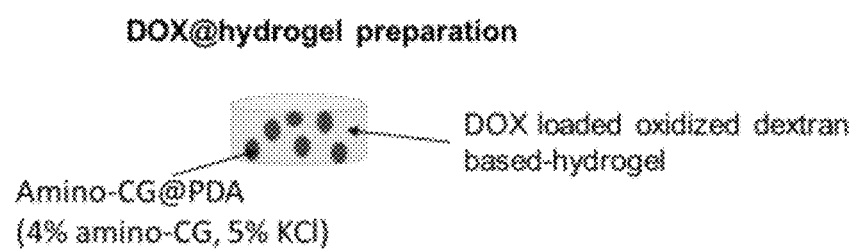
FIG. 14 is an explanatory view of a hydrogel having PDA-containing aminated carrageenan composite gel beads embedded in a hydrogel containing doxorubicin hydrochloride (DOX)

FIG. 14 shows an explanatory view of the hydrogel having the PDA-containing aminated carrageenan composite gel beads embedded in the hydrogel containing doxorubicin hydrochloride (DOX).

Figure 15:
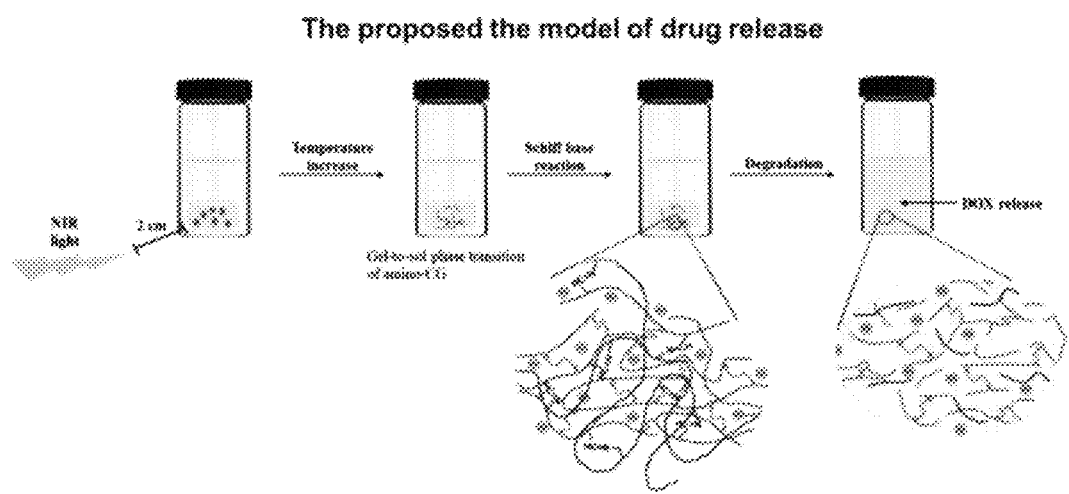
FIG. 15 is an explanatory view showing that a hydrogel having PDA-containing aminated carrageenan composite gel beads embedded in a hydrogel containing doxorubicin hydrochloride (DOX) is irradiated with NIR light, the PDA-containing aminated carrageenan composite beads are dissolved, and amino groups are exposed, whereby the hydrogel for Ox-Dex-GMA is decomposed to result in releasing of doxorubicin hydrochloride (DOX) in the hydrogel.

FIG. 15 shows an explanatory view showing that the hydrogel having the PDA-containing aminated carrageenan composite gel beads embedded in the hydrogel containing doxorubicin hydrochloride (DOX) is irradiated with NIR light to dissolve the PDA-containing aminated carrageenan composite gel beads to expose the amino groups, thereby decomposing the hydrogel for Ox-Dex-GMA, and releasing doxorubicin hydrochloride (DOX) in the hydrogel.

Figure 16:
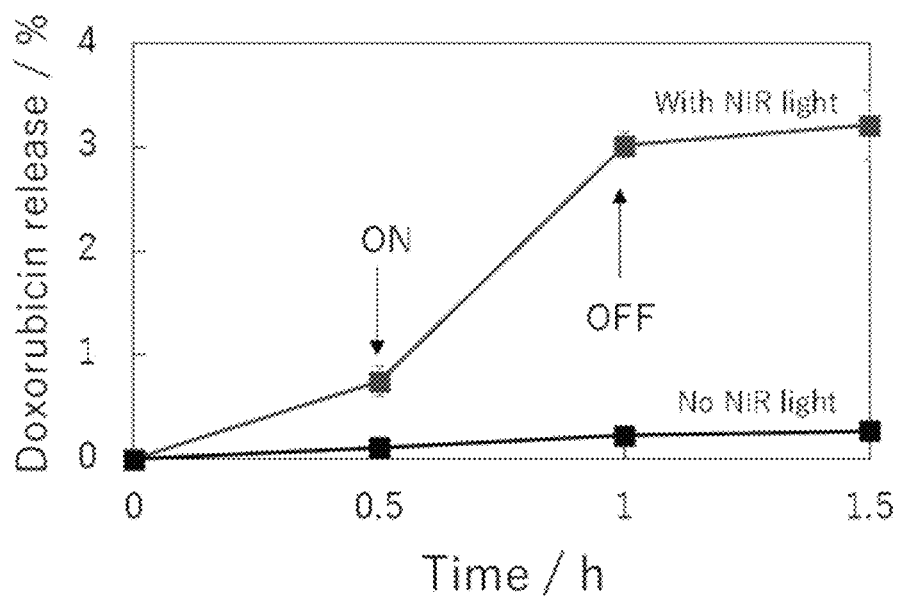
FIG. 16 is a graph showing changes in amounts of doxorubicin hydrochloride (DOX) released in the cases where NIR light irradiation is turned ON (irradiated) or turned Off (not irradiated).

FIG. 16 is a graph showing changes in amounts of doxorubicin hydrochloride (DOX) released in cases where NIR light irradiation is turned ON (irradiated) and turned OFF (not irradiated). The amount of DOX released rapidly increased when the irradiation was turned on after 0.5 hours, and the rapid increase of the amount of DOX released stopped when it was turned off after 1.0 hour. Further, by repeating ON and OFF after 1.5 hours, the average amount of DOX released could be maintained in an appropriate range.

INDUSTRIAL APPLICABILITY

According to the present invention, a photodegradable hydrogel can be obtained. The present invention is an industrially useful invention.

The invention claimed is:

1. An additive for photodegradable hydrogels, the additive comprising aminated carrageenan gel beads with embedded polydopamine particles.

2. A method for producing an additive for photodegradable hydrogels, the method comprising a step of adding an aqueous solution of potassium salt, sodium salt or calcium salt in which polydopamine particles are dispersed to an aqueous solution of aminated carrageenan, where the additive comprises aminated carrageenan gel beads with embedded polydopamine particles.

3. A hydrogel having a modified α-glucan crosslinked by dithiothreitol, the modified α-glucan comprising:

at least one group represented by the following formula II:

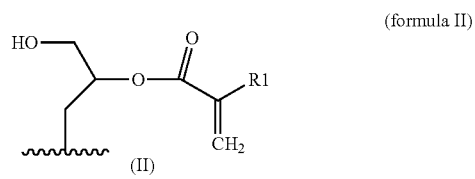

(formula II)

in which the R1 group is a C1-C3 alkyl group,
the at least one group represented by the formula II being introduced into α-glucan having a weight average molecular weight in a range of from 2,000 to 200,000 at a degree of substitution in a range of from 10 to 50% per glucose unit of the α-glucan, wherein H of an OH group in the α-glucan is substituted with the group represented by the formula II; and
at least one aldehyde group resulting from oxidation of periodic acid, the at least one aldehyde group being introduced at a degree of substitution in a range of from 25 to 75% per glucose unit of the α-glucan,
wherein aminated carrageenan gel beads with embedded polydopamine particles are embedded in the hydrogel.

4. The hydrogel according to claim 3, wherein a drug is embedded in the hydrogel.

5. The hydrogel according to claim 3, wherein the α-glucan having the weight average molecular weight in the range of from 2,000 to 200,000 is dextran.

6. A method for producing a photodegradable hydrogel, comprising the steps of:

allowing α-glucan having a weight average molecular weight in a range of from 2,000 to 200,000 to react with a compound represented by the following formula I:

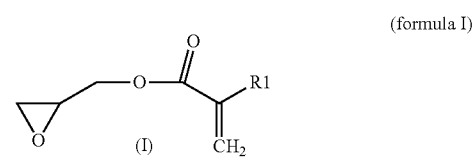

(formula I)

in which the R1 group is a C1-C3 alkyl group,
to introduce at least one group represented by the following formula II:

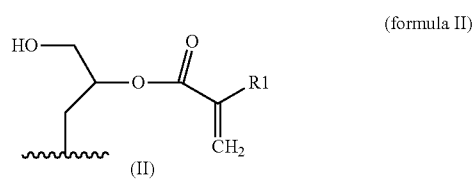

(formula II)

in which the R1 group is the same group as the R1 group in the formula I,
into the α-glucan;
oxidizing the α-glucan having the introduced group represented by the formula II with periodic acid or a periodate to introduce at least one aldehyde group into the α-glucan and form a gelling agent; and adding aminated carrageenan gel beads with embedded polydopamine particles to the gelling agent, and causing a crosslinking reaction with a polythiol reducing agent to form a hydrogel.

7. The method according to claim 6, wherein the aminated carrageenan gel beads with embedded polydopamine particles are prepared by a method comprising a step of adding to an aqueous solution of aminated carrageenan an aqueous solution of potassium salt, sodium salt or calcium salt wherein polydopamine particles are dispersed.

8. The method according to claim 6, wherein the step of adding the aminated carrageenan gel beads with embedded polydopamine particles to the gelling agent, and causing the crosslinking reaction with the polythiol reducing agent to form the hydrogel is a step of adding a drug and the aminated carrageenan gel beads with embedded polydopamine particles to the gelling agent, and causing the crosslinking reaction with the polythiol reducing agent to form the hydrogel.

9. A method for photo-releasing a drug from a hydrogel, comprising irradiating the photodegradable hydrogel produced by the method according to claim 8 with light.

10. A method for photodegrading a hydrogel, comprising irradiating the photodegradable hydrogel produced by the method according to claim 6 with light.

* * * * *